United States Patent
Walkow

(10) Patent No.: US 6,794,652 B2
(45) Date of Patent: Sep. 21, 2004

(54) METHOD AND APPARATUS FOR A RIGID BACKUP LIGHT SOURCE FOR DOWN-HOLE SPECTRAL ANALYSIS

(75) Inventor: Arnold M. Walkow, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 0 days.

(21) Appl. No.: 10/265,991

(22) Filed: Oct. 7, 2002

(65) Prior Publication Data

US 2003/0094575 A1 May 22, 2003

Related U.S. Application Data

(63) Continuation-in-part of application No. 09/574,324, filed on May 19, 2000, now abandoned.

(51) Int. Cl.[7] .................................................. G01V 8/00
(52) U.S. Cl. ....................................... 250/343; 250/256
(58) Field of Search ................................ 250/343, 253, 250/254, 256

(56) References Cited

U.S. PATENT DOCUMENTS

| | | | |
|---|---|---|---|
| 4,994,671 A | | 2/1991 | Safinya et al. |
| 5,872,655 A | * | 2/1999 | Seddon et al. ............... 359/588 |
| 6,437,326 B1 | * | 8/2002 | Yamate et al. ........... 250/269.1 |

* cited by examiner

*Primary Examiner*—Constantine Hannaher
*Assistant Examiner*—Timothy J. Moran
(74) *Attorney, Agent, or Firm*—Madan, Mossman & Sriram, P.C.

(57) ABSTRACT

A rigid redundant light source for obtaining down hole near infrared data in a NIR data acquisition instrument is provided having a plurality of lamps positioned in close proximity and symmetrically about a common optical axis. A lens system for capturing and collimating the light is provided. The structure is arranged and dimensioned so that a single collimating lens can be used for a plurality of light sources. A switch and sensor is provided for turning on an alternate light source when a first light source burns out. A filter is rotated 90 degrees with respect to the light sources to minimized off axis error when switching between light sources.

18 Claims, 3 Drawing Sheets

METHOD AND APPARATUS FOR A RIGID BACKUP LIGHT SOURCE FOR DOWN-HOLE SPECTRAL ANALYSIS

CROSS REFERENCE TO RELATED APPLICATION

This patent application is a continuation in part of and claims priority from U.S. patent application Ser. No. 09/574,324 entitled Rigid Backup Light Source for Down-Hole Spectral Analysis by Arnie Walkow, filed on May 19, 2000 now abandoned.

FIELD OF THE INVENTION

The present invention relates generally to the field of down hole near infrared spectral analysis of formation fluids and in particular to rigid redundant light source for near infrared spectral analysis having a single collimating lens.

BACKGROUND OF THE RELATED ART

Conventional near infrared spectral analysis tools provide a light source for supplying infrared energy for spectral analysis. The light source is usually an incandescent bulb which is aligned to focus light on a down hole fluid analysis for obtaining either absorbent or reflectance spectral data. Near infra spectral data gathering instruments and the associated light sources are well known in the art. See, for example, U.S. Pat. No. 4,994,671, by Safinya et al., entitled, Apparatus and Method for Analyzing the Composition of Formation Fluids.

There is no known prior art for rigidly mounting more than one efficient optical lamp source array in a minimum packaging configuration which will satisfactorily serve a single collimating lens with a common optical axis. One application where this need arises is in providing more than one light source for a single detector for spectral analysis.

There is a current need for down hole near infrared spectral analysis tool, which inherently involves the use of a light source. Small, efficient, low wattage, high output commercially available light sources are inherently more prone to failure than the electronic detection devices used for spectral analysis. It is therefore prudent to provide a back-up light source or sources to avoid abandoning a job when a single lamp fails and the crew is forced to return to the base to replace the light source. In the early stages of introducing a tool to the field, back-up tools may not be available on all jobs and thus will not be a reality. Moreover, a customer could be discouraged and might not be anxious to make a second trip in the bore hole for NIR data.

An alternative is to provide a redundant light source on a rotary motor that rotates the expended light source out of alignment with the down hole sample and rotates the redundant lamp into alignment. The problem with utilizing such an electric motor is that it expends power in a limited power budget provided by a down hole power supply or battery. The electric motor also adds to the complexity and weight of a down hole tool. Another alternative is to utilize a prism or special bulb developed with multiple filaments feeding a single, large lens, however, such a design is complex and a cracked bulb or lead seal might cause all the filaments to fail simultaneously. Thus there is a need for a simple redundant light source that does not deplete the down hole power supply or require rotation of the redundant light source.

SUMMARY OF THE INVENTION

The present invention provides a rigid redundant light source for obtaining down hole near infrared data. Primary and second light sources, collimating lens, sample tube and filter are provided and positioned to minimize off-axis errors caused by mounting two light sources symmetrically about the optical axis of collimating beam. A rigid redundant light source for obtaining down hole near infrared data in a NIR data acquisition instrument is provided having a plurality of lamps positioned in close proximity to each other and symmetrically about a common optical axis for a single collimating lens. A single collimating lens system for capturing and collimating the light is provided. The structure is arranged and dimensioned so that a single collimating lens can be used for a plurality of light sources with affecting the data. A switch and sensor is provided for turning on an alternate light source when a first light source burns out. A filter is rotated 90 degrees with respect to the light sources to minimized off axis error generated when switching between light sources.

A plurality of small diameter light sources are positioned close together an optimal distance from the single collimating lens to enable the use of a single lens for more than one light source.

DETAILED DESCRIPTION OF THE PREFERRED EMBODIMENT

Figure 1:
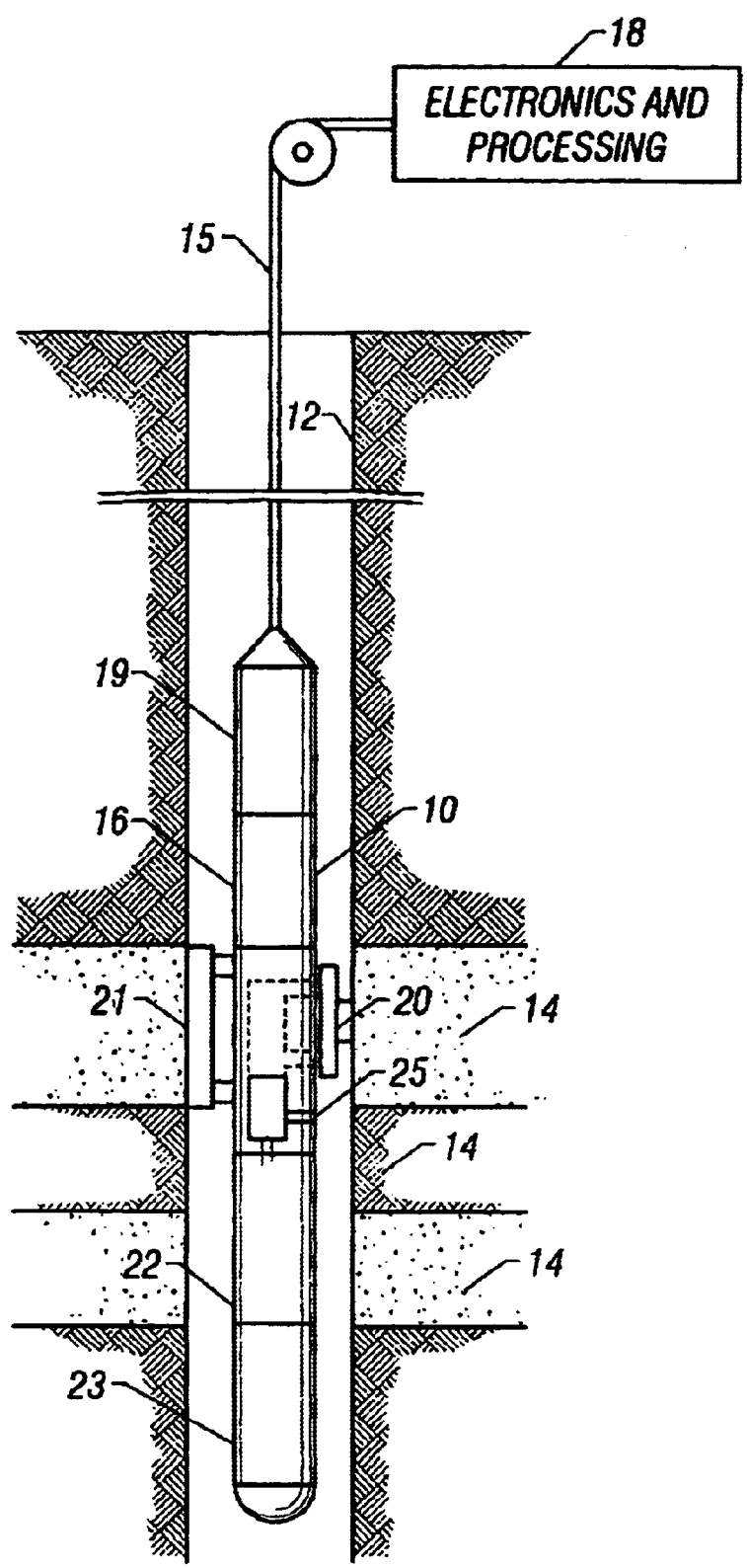
FIG. 1 is a schematic diagram of down hole near infrared apparatus for analyzing the composition of a formation fluid.

FIG. 1 illustrates a schematic diagram for a conventional down hole near infrared (NIR) apparatus for analyzing the composition of a formation fluid. The bore hole logging tool 10 for testing earth formations and analyzing the composition of fluids from the formation 14 is seen in FIG. 1. As illustrated, the tool 10 is suspended in the borehole 12 from the lower end of a typical multiconductor cable 15 that is spooled in the usual fashion on a suitable winch (not shown) on the formation surface. On the surface, the cable 15 is electrically connected to an electrical control system 18. The tool 10 includes an elongated body 19, which encloses the down hole portion of a tool control system 16. The elongated body 19 also carries a selectively extendible fluid admitting assembly 20 and a selectively extendible tool-anchoring member 21 which are respectively arranged on opposite sides of the body. The fluid admitting assembly 20 is equipped for selectively sealing off or isolating selected portions of the borehole 12 wall such that fluid communication with the adjacent earth formation is established. Also included with tool 10 are a fluid analysis module 25 through which the obtained formation fluid flows. The fluid may thereafter be expelled through a port (not shown) or it may be sent to one or more fluid collecting chambers 22 and 23, which may receive and retain the fluids obtained from the formation. Control of the fluid admitting assembly, the fluid analysis section, and the flow path to the collecting chambers is maintained by the electrical control systems 16 and 18. Additional details of methods and apparatus for obtaining formation fluid samples may be had by reference to U.S.

Pat. No. 3,859,851 to Urbanosky and U.S. Pat. No. 4,396,259. It should be appreciated, however, that it is not intended that the invention be limited to any particular method or apparatus for obtaining the formation fluids.

Figure 2:
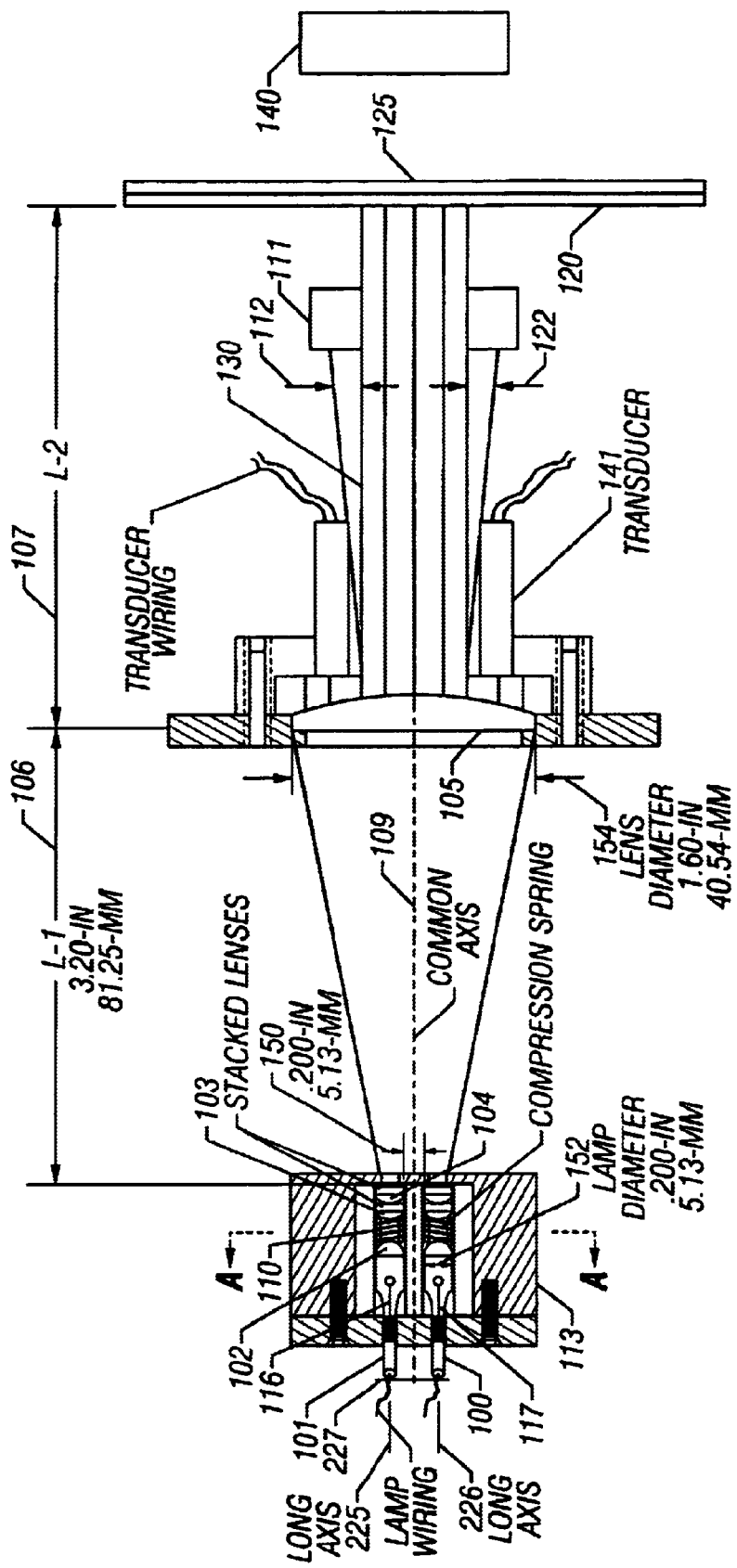
FIG. 2 is a side view of a cross sectional view of a preferred embodiment of the present invention.

Turning now to FIG. 2, the present invention provides a structure for providing multiple light sources arranged symmetrically about a common optical axis of a collimated light beam 130 incident upon a fluid sample in tube 111, optical filter 125 and optical wavelength transducer/data acquisition/analysis system 140, as shown in FIG. 2. The present invention provides an efficient, small, high intensity rigid redundant light source that is environmentally durable at a variety of operating voltages. Lamp life can range from hundreds of hours to thousands of hours, depending upon the driving voltage, voltage ramp up and current limitation. System design considerations to arrive at the suitability for the application are the off-axis error or proximity of the lamp centerlines to the common optical axis, the distance 106 between the lamps 116 and 117 and associated lenses 103 and 104 to the single collimating lens 105, and the distance 107 from the collimating lens to the optical target.

As shown in FIG. 2, the critical dimensions for enabling the present invention to operate are detailed. The vertical separation distance 150 between the outside diameter of each of two horizontally oriented lamps 116 and 117 is 0.045 inches or 1.13 mm. The distance 106 between the last stacked lens for the lamps 116 and 117 to the collimating lens 105 is 3.20 inches or 81.25 mm. The diameter of the collimating lens is 1.60 inches or 40.54 mm. The diameter of each lamp 116 and 117 is 0.200 inch or 5.13 mm. It is the combination of spatial and angular relationships of the lamps, lens, filters and sample tube that enable the present invention to perform with a single collimating lens, that is, the relationship of the diameter of the lamps 116 and 117 to the diameter of the collimating lens 105, the relationship of the distance between the lamps 150 to the diameter of the lamps 152, the relationship between the vertical separation distance 150 between the lamps and the distance 106 from the lamps to the collimating lens that enables the multiple-lamp system to function with a single collimating lens with a minimal off axis error when switching between lamp 116 and 117. In a preferred embodiment, the ratio of the diameter of each lamp 116 or 117 to the diameter 154 of the collimating lens is 1/8.

FIG. 2 illustrates two lamps 116 and 117, in close proximity to common optical axis 109. The first lamp is used as a light source until it burns out and the second lamp is turned on. The absence of data from transducer 140 or 141 indicates that a light source has burned out. The distance between the longitudinal axes 225, 266 of lamp 116 or 117, respectively, and common optical axis 130 is referred to as the off-axis error. The off-axis error causes a change 112 in beam 130 location of a maximum of 2.6 degrees 112, when changing from the first lamp 116 to the second lamp 117. Each lamp has an integral lens 102 in close proximity to the filament. The lamp lens acquires a large portion of, but less than 50 per cent, the light radiation envelope emitted from the heated lamp filament. A lens 102 is provided and positioned as shown in FIG. 2, to obtain the beam geometry projected at distance 106 L-1 to the collimating lens. Alternative lens arrangements and orientations are shown in FIGS. 5A–5E. A preferred embodiment utilizes a single lens as show in FIG. 5E.

The distance 106 from the lamps 116 and 117 to the single collimating lens and the distance 107 from the collimating lens to the detector determine the acceptability of the detection error introduced by off-axis error introduced by offsetting the lamps 116 and 117 from the common optical axis 109. In a preferred embodiment fluid sample tube 111, blocker 120 and filter 125 are elongated in the vertical direction. The light source housing 113 is rotated so that a line passing through the longitudinal axes of light source 116 and light source 117 is rotated ninety degrees from the longitudinal axis of the linear variable filter (such as a filter with linearly varying input sensitivity along the longitudinal filter axis). Such 90 degree rotation of the light source housing and associated light sources with respect to the linear variable filter substantially eliminates the effects of amplitude variations and data shifting due to the off-axis error.

The collimated light source beam 130 has its highest amplitude on or near the optical axis 109 and decreases slightly in amplitude as the distance from the optical axis increases. As the longitudinal axis of a light source moves away from the optical axis 109 of the collimating lens 105, the off axis error increases. As the light source moves in a first direction away from the optical axis, the collimated amplitude peak moves in the opposite direction. The off axis error and associated peak variation occurs along a line passing through the center of the longitudinal axes of the first and second light source 116 and 117. Light source 116 generates off-axis error 122 and light source 117 generates off-axis error 112. These amplitude variations induce a shift in the data obtained through undesirable variations in the amplitude of light incident upon the sample tube and the linear variable filter. The amplitude shift and associated data shift are at a maximum when the longitudinal axis of the filter is parallel to a line passing through the longitudinal axes of light sources 116 and 117. The amplitude shift and associated data shift are at a minimum when the longitudinal axis of the filter is orthogonal to a line passing through the longitudinal axes of light sources 116 and 117.

Such changes occur when switching from the first light source to the second light source due to each light source having a different position relative to the optical axis of the collimating lens and thus striking the filter a different location. The shifts between light sources can cause shifts in the data, which are not due to the properties of the fluid in the sample tube. This phenomenon may generate unexplained changes in a near infrared data when the second light source 117 replaces the first light source 116. Thus, to avoid data shifts or changes and to obtain substantially uniform light intensity incident upon the sample tube 111, filter 125 and transducer 140, whether using the first light source 116 or the second light source 117, the light source housing 113 is rotated 90 degrees from the longitudinal axis of the sample (221) and the longitudinal axis of the filter (220). This rotation minimizes or substantially eliminates any variation in light amplitude incident upon the sample, filter and transducer when changing between the first light source one and the second light source. The maximum off axis error induced in the collimated light beam is less detrimental to light amplitude uniformity in the narrow dimension across the width of the elongated sample tube and filter, than it would be in the longer dimension along the length of the elongated sample tube and filter.

Figure 3:
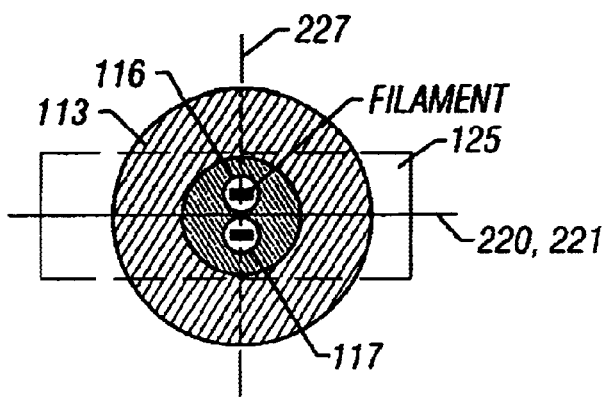
FIG. 3 is a cross sectional view of the lamp mounting arrangement for a preferred embodiment.
Figure 4A:
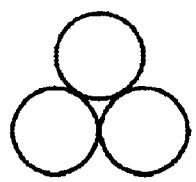
FIGS. 4A–4E illustrate alternative embodiments of multiple lamp configurations for the present invention.
Figure 4B:
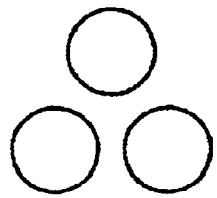
Figure 4C:
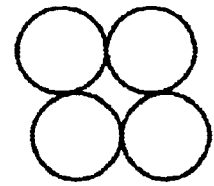
Figure 4D:
Figure 4E:
Figure 5A:
FIGS. 5A–5E illustrate alternative preferred multiple lens configurations for the present invention.
Figure 5B:
Figure 5C:
Figure 5D:
Figure 5E:

FIG. 3 is a cross-section of the preferred light source housing taken orthogonal to the longitudinal axes of the light source housing 113 and the first and second light sources, 116 and 117. FIGS. 4A–4E illustrates alternative embodiment configurations for multi-bulb spacing and arrays. FIGS. 5A–5E illustrates alternative lens configurations and shapes for a preferred embodiment.

The foregoing description is for illustration purposes only and should not be considered as a limitation upon the scope of the invention, which is determined by the following claims.

What is claimed is:

1. An apparatus for providing an alternate light source for illuminating a fluid sample in a near infrared data acquisition instrument comprising:

a near infrared data acquisition instrument for traversing a well bore;

a fluid sample container in the near infrared data acquisition instrument for containing a fluid sample;

a first light source for illuminating the fluid sample in the sample container;

a second light source for illuminating the fluid sample in the sample container;

a single collimating lens having an optical axis for collimating light from the first light source and the second light source; and a mounting block for positioning the first light source and the second light source symmetrically about the optical axis of the collimating lens for symmetrically illuminating the fluid sample container from the first light source and the second light source to reduce off-axis data errors.

2. The apparatus of claim 1 wherein the first light source and the second light source are located in close proximity to the optical axis of the collimating lens to reduce amplitude variations in light incident upon a linear variable filter positioned on the opposite side of the sample from the light source.

3. The apparatus of claim 1 further comprising an optical filter positioned on the opposite side of the fluid sample from the first and second light source so that light from the light source passes through the fluid sample and is incident upon the optical filter.

4. The apparatus of claim 3 wherein the optical filter further comprises:

a longitudinal axis for the optical filter, the longitudinal axis of the optical filter rotated 90 degrees from a line perpendicular to the optical axis and passing through a longitudinal axis for the first light source and a longitudinal axis for the second light source in order to minimize off-axis errors in data.

5. The apparatus of claim 3 wherein the fluid sample container further comprises:

a sample tube having a longitudinal axis aligned with a longitudinal axis for the optical filter wherein the longitudinal axis of the sample container is rotated 90 degrees from a line perpendicular to the optical axis and passing through a longitudinal axis of the first light source and a longitudinal axis of the second light source in order to minimize off-axis errors in data.

6. The apparatus of claim 1, further comprising:

a diameter for the light source;

a diameter for collimating lens, wherein the relationship of the diameter of the light source to the diameter of the collimating lens is 1 to 8.

7. The apparatus of claim 1, further comprising:

a vertical separation distance between first and second light sources symmetrically positioned about the optical axis for the collimating lens; and a distance from the light source to the collimating lens, wherein the relationship between the vertical separation distance between the light sources and the distance from the light sources to the collimating lens is substantially 1 to 71.

8. The apparatus of claim 1, further comprising:

a diameter for the light source symmetrically positioned about the optical axis for the collimating lens; and a distance from the light source to the collimating lens, wherein the relationship between the diameter of the light source and the distance from the light sources to the collimating lens is 1 to 16.

9. The apparatus of claim 1, further comprising:

a data sensor for determining when the first light source burns out;

a switch for turning on the second light source, which was initially turned off, for illuminating the sample container when the first light source burns out.

10. A method for providing an alternate light source for illuminating a fluid sample in a near infrared data acquisition instrument comprising:

traversing a well bore with a near infrared data acquisition instrument;

obtaining a fluid sample container in the near infrared data acquisition instrument;

illuminating the fluid sample with a first light source;

alternatively illuminating the fluid sample with a second light source;

collimating the light source with a single collimating lens having a single optical axis for collimating light from the first light source and the second light source; and positioning the first light source and the second light source symmetrically about the optical axis of the collimating lens for symmetrically illuminating the fluid sample container from the first light source and the second light source to reduce off-axis data errors.

11. The method of claim 10, further comprising:

positioning the first light source and the second light source in close proximity to the optical axis of the collimating lens to reduce amplitude variations in light incident upon a linear variable filter positioned on the opposite side of the sample from the light source.

12. The method of claim 10 further comprising:

sensing light from the first and second light source passing though the fluid sample to an optical filter positioned on the opposite side of the fluid sample so that light from the light source passes through the fluid sample and is incident upon the optical filter.

13. The method of claim 12, further comprising:

rotating a longitudinal axis for the optical filter 90 degrees with respect to a line perpendicular to the collimating lens optical axis optical axis and passing through a longitudinal axis for the first light source and a longitudinal axis for the second light source in order to minimize off-axis errors in data when switching from the first light source to the second light source.

14. The method of claim 12 further comprising:

rotating a sample tube having a longitudinal axis with respect to a longitudinal axis for the optical filter wherein the longitudinal axis of the sample container is rotated 90 degrees with respect to a line perpendicular to the optical axis and passing through a longitudinal axis of the first light source and a longitudinal axis of the second light source in order to minimize off-axis errors in data.

15. The method of claim 10, further comprising:

selecting a diameter for the light source and a diameter for collimating lens, wherein the relationship of the diameter of the light source to the diameter of the collimating lens is approximately 1 to 8.

16. The apparatus of claim 10, further comprising:

a vertical separation distance between first and second light sources symmetrically positioned about the optical axis for the collimating lens; and a distance from the light source to the collimating lens, wherein the relationship between the vertical separation distance between the light sources and the distance from the light sources to the collimating lens is approximately 1 to 71.

17. The method of claim 10, further comprising:

selecting a diameter for the light source symmetrically positioned about the optical axis for the collimating lens; and positioning the light source a distance from the collimating lens, wherein the relationship between the diameter of the light source and the distance from the light sources to the collimating lens is approximately 1 to 16.

18. The method of claim 10, further comprising:

determining when the first light source burns out; and turning on the second light source, which was initially turned off, for illuminating the sample container when the first light source burns out.

* * * * *